United States Patent [19]

Kleiser et al.

[11] Patent Number: 4,807,498
[45] Date of Patent: Feb. 28, 1989

[54] BLIND FASTENER INSTALLATION TOOL AND MODIFIED FASTENER

[75] Inventors: Charles M. Kleiser; Mahen S. Gala, both of Warminster, Pa.

[73] Assignee: SPS Technologies, Inc., Newtown, Pa.

[21] Appl. No.: 921,650

[22] Filed: Oct. 21, 1986

[51] Int. Cl.$^4$ ............................................. B25B 13/50
[52] U.S. Cl. ............................................. 81/56; 81/434
[58] Field of Search .................. 81/56, 55, 434, 57.32, 81/57.14, 13, 57.30, 433

[56] References Cited

U.S. PATENT DOCUMENTS

| 3,850,055 | 11/1974 | Triplett | 81/56 |
| 4,428,261 | 1/1984 | Takatsu | 81/434 |
| 4,630,510 | 12/1986 | Belanger | 81/55 |

Primary Examiner—James G. Smith
Attorney, Agent, or Firm—James D. Dee; Aaron Nerenberg

[57] ABSTRACT

A blind fastener installation tool as well as a blind fastener and a core bolt for the blind fastener, both being adapted for use with the installation tool. The installation tool has coaxially disposed first and second tool engagement members each engageable at one of their ends, respectively, with a drive stem of a core bolt of the blind fastener, and a bearing surface forming element of the blind fastener, and an axial through passageway through the first tool member for removal of the drive stem from the tool at a location remote from the engagement ends of the tool engagement members. The core bolt has an elongated main body having a head at one end, a taper at the other end, a breakneck therebetween, and an elongated drive configuration extending along the entire portion of the core bolt between the breakneck and the taper.

14 Claims, 1 Drawing Sheet

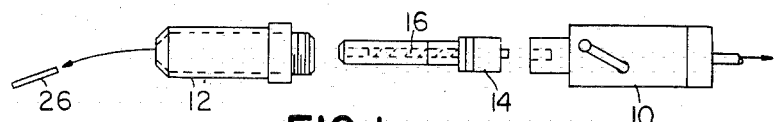
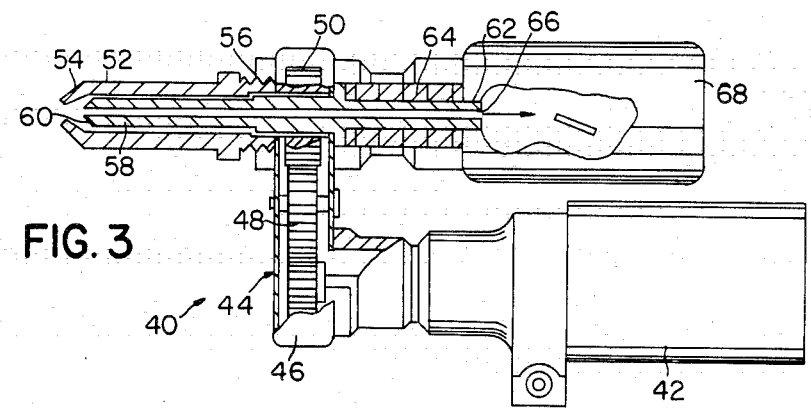
FIG. 3
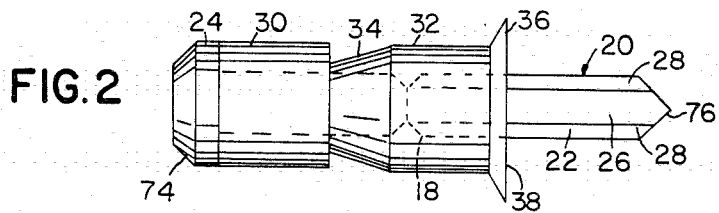
FIG. 2
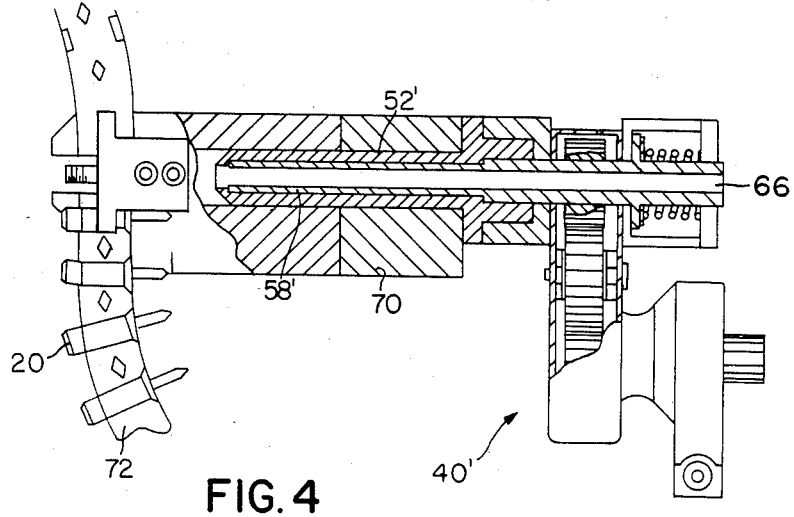
FIG. 4

BLIND FASTENER INSTALLATION TOOL AND MODIFIED FASTENER

BACKGROUND OF THE INVENTION

The present invention relates to fasteners and to fastener installation tools and more particularly to threaded blind fasteners and to installation of threaded blind fasteners.

Blind fasteners generally use one of two basic techniques to accomplish the installation process. The first technique involves applying pulling force to a mandrel which expands a sleeve to form a bearing surface on the blind side of the joint. The second technique involves applying a rotational force to a threaded core bolt such as to cause the sleeve to be advanced and expanded. The present invention is directed to improvements in tools for installing rotatably installed blind fasteners, although certain features of the invention will have broader application and, therefore, the claims are not intended to be limited to rotatably driven fasteners unless explicitly recited therein.

Numerous hand tools are available to install threaded blind fasteners, including pneumatic handheld tools in either pistol or right angle driver configurations, and hand operated ratchet tools.

SUMMARY OF THE PRESENT INVENTION

The present invention provides an improved core bolt for a blind fastener, an improved blind fastener, and an improved blind fastener installation tool.

The installation tool includes a wrench adapter having a through axial passage, a nose adapter mounted coaxially with the wrench adapter, and a drive mechanism for driving the wrench adapter relative to the nose adapter. The wrench adapter engages the drive stem of a blind fastener while the nose adapter engages the bearing surface forming element of the blind fastener. Upon completion of the installation of a blind fastener, the drive stem breaks and is free to travel along the through axial passage of the wrench adapter for removal.

In the preferred embodiment, the wrench adapter and the nose adapter are relatively driven rotationally and the blind fasteners are automatically sequentially delivered to the wrench and nose adapter. Furthermore, in the preferred embodiment, a collection receptacle or bottle is provided at one end of the axial passage to temporarily store the discarded drive stems.

The blind fastener includes a core bolt having a main body with a head and a taper formed at its opposite ends and a breakneck groove disposed therebetween. An elongated drive portion, preferably an elongated drive flat, extends the entire length of the drive stem portion of the core bolt from the taper to the breakneck. In the preferred embodiment, the head is chamfered, the taper is a point, and the portion of the core bolt between the head and the breakneck groove is threaded.

A primary object of the present invention is to provide an improved method and device for installing blind fasteners, especially rotatably driven blind fasteners, providing faster installation rates.

Another object of the present invention is to provide a method and device for automatically installing plurality of blind fasteners, especially rotatably driver blind fasteners.

Still another object of the present invention is to provide a method and device for automatically disposing of drive stems from blind fasteners after the fasteners have been installed.

Yet another object of the present invention is to provide a method and device for installing blind fasteners which method and device minimizes the handling of the fasteners and thereby protects the fasteners from contaminants and from being damaged.

Still yet another object of the present invention is to provide a blind fastener adapted for automated installation.

These and many other objects, features, and advantages of the present invention will become apparent to those skilled in the art when the following exemplary detailed description of the present invention is read in conjunction with drawings appended hereto.

BRIEF DESCRIPTION OF THE DRAWING

In the drawings, wherein like reference numerals refer to like elements throughout:

FIG. 1 depicts a schematic exploded view of a portion of a prior art blind fastener installation tool;

FIG. 2 shows a side elevational view of a blind fastener to be installed by the installation tool of the present invention;

FIG. 3 is a partially cut away partial side view of a first example of a blind fastener installation tool according to the present invention; and FIG. 4 is a partially cut away partial side view of a second example of a blind fastener installation tool according to the present invention.

DETAILED DESCRIPTION OF THE PRESENT INVENTION

Referring now to the drawing and more particularly to FIG. 1 thereof, a schematic view of the prior art installation tool 10 for installing a threaded blind fastener is schematically depicted. The installation tool 10, as is well known in the art, includes a nose adapter 12 concentrically disposed with a wrench adapter 14. The nose adapter 12 is provided with an ejector spring 16 for ejecting drive stems 26, described below, of blind fasteners installed using the installation tool 10.

FIG. 2 depicts a threaded blind fastener 20, well known in the art, including a core bolt 22 having an enlarged head 24 at one end, a drive stem 26 at the other end an externally threaded portion, not shown, between the enlarged head 24 and the drive stems 26 drive flats 28 on the drive stem 26, and a breakneck disposed between the externally threaded portion and the drive stem 26. A sleeve 30 is rotatably mounted to the core bolt 22 adjacent the enlarged head 24. An internally threaded expander nut 32 is threaded onto the externally threaded portion of the core bolt 24. The expander nut 32 has a nose portion 34 abutting the sleeve 30, an enlarged head 36 remote from the nose portion 34, and drive means, not shown, on a transverse surface 38 adjacent the nose portion 34.

As is well known in the art, when the blind fastener 20 is to be installed to form a joint using the prior art installation tool 10, the blind fastener 13 first passed through a bore in a workpiece, not shown, until the enlarged head 36 of the expander nut 32 abuts the work piece. The wrench adapter 14 is engaged with the drive flats 28 of the drive stem 26 while the nose adapter 12 is simultaneously engaged with the drive means on the transverse surface 38 of the expander nut 32.

The installation tool 10 is operated to rotatably drive the core bolt 22 relative to the expander nut 32, causing the nose portion 34 of the expander nut to advance towards the enlarged head 24 of core bolt, thereby expanding the sleeve 30 on the blind side of the workpiece to form bearing surface. The continued relative rotation of the core bolt 22 and the expander nut 32 draws the sleeve 30 against the work piece to preload the joint. At a torque level determined by the geometry of the breakneck and the strength of the core bolt 22, the core bolt 22 breaks at the breakneck 18 and the installation of the blind fastener is complete.

When the prior art installation tool 10 is disengaged from the blind fastener, the spring 16 of the wrench adapter 14 ejects the drive stem 26, which must be swept up later.

A first example of an installation tool 40 according to the present invention is shown in FIG. 3 of the drawing.

A power tool 42, well-known in the art and therefore not shown in detail, is connected to a gear assembly 44 consisting of a housing 46, a driving gear 48 and a driven gear 50; whereby the driven gear 50 is rotatably driven by the power tool 42.

A hollow nose adapter 52 is interconnected with the housing 46. The end 54 of the nose adapter 52 is provided with a wrenching means engageable with the drive means on the transverse surface 38 of the expander nut 32. Preferably, the nose adapter 52 is threadably engaged with the housing 46 as shown at 56 to permit quick removal of a nose adapter of one size and replacement with one of another size.

A wrench adapter 58 is disposed within a portion of the housing 46 and extends axially through the driven gear 50 and a portion of the nose adapter 52. The wrench adapter 58 is constrained, for example by a key, not shown, to rotate with the driven gear 50. The end 60 of the wrench adapter 58 located proximate the wrenching means end 54 of the nose adapter is provided with wrenching means engageable with the drive flats 28 of the core bolt 22 of the blind fastener 20. The other end 62 of the wrench adapter 58 is interconnected with the housing 46 by means of a torque drive spring 64. The wrench adapter 58 is further provided with an axial passageway 66 for a purpose to be described shortly.

A collection reservoir an bottle 68 is preferably removably connected to the portion of the housing 46 adjacent the end 62 of the wrench adapter 58. The collection reservoir is hollow and communicates with the axial passageway 66 for a purpose to be described shortly.

As will be appreciated by those skilled in the art, the installation tool 40 is operated similarly to the prior art installation tool 10 by engaging the wrench adapter 58 with drive flats 28 of the drive stem 26 and engaging the nose adapter 52 with the expander nut 32. However, when the installation is complete and the breakneck 16 of the blind fastener breaks, the drive stem 26 temporarily remains within the axial passageway 66 of the wrench adapter 58. The drive stem 26 will slide along the axial passageway 66 into the bottle if the installation tool 40 is tilted or, alternatively, will be advanced into the bottle by the core bolt 22 of the next blind fasteners 20 to be installed.

It will be appreciated by those skilled in the art that the improved installation tool 40 of the present invention permits more rapid installation of the blind fasteners 20 than the prior art installation tool 10 since there is no need to wait until the previous drive stem 26 is ejected before installing the next fastener. This advantage also facilitates automatic feeding of the fasteners, as will be described shortly. Furthermore, the removable reservoir or bottle 68 reduces the hazard and the mess which previously existed with discarded drive stems 26 being ejected into the work area.

Referring now to FIG. 4, a second example of a blind fastener installation tool 40' according to the present invention is illustrated. The second installation tool 40' differs from the first installation tool 40 in that a transfer mechanism 70 is mounted to the nose adapter 52. A belt 72 having a series of blind fasteners 20 mounted thereto is fed through the transfer mechanism 70 to deliver the blind fasteners sequentially into alignment with the wrench adapter 58' and the nose adapter 52'. The details of the transfer mechanism 70 are not shown in detail as there are numerous suitable transfer mechanisms well-known to those skilled in the art which may readily be used to deliver fasteners to a tool.

The installation tool 40' permits rapid installation of a plurality of blind fasteners 20' and reduces the amount of operator handling of the fasteners. If desired, the belt 72 may be provided with differing blind fasteners 20 in a preselected sequence.

To facilitate operation of the installation tool 40', it has been found beneficial to provide a chamfer 74 on the core bolt head to facilitate entry of the blind fastener 20 into a bore in a workpiece, since the chamfer cooperates with the workpiece to position the fastener. Furthermore, it is preferable to provide a point 76 on the drive stem 26 of the bolt to facilitate alignment of the drive stem with the axial passageway 66' of the wrench adapter 58'. Finally, it should be noted that the drive flats 28 must extend the entire length of the drive stem 26. The novel features of the blind fastener greatly reduce positioning errors and thus render the installation tool 40' significantly more efficient.

The above detailed description includes the best mode for carrying out the invention contemplated by the inventor at the time of filing the present invention. It will be appreciated by those skilled in the art that man modifications may be made to the installation tools 40 and 40' or the fastener 20 of the present invention without departing from the spirit of the present invention. In particular, it will be appreciated that the features of the present invention can be applied to any suitable fastener having a drive stem 26. Such modifications are included within the intended scope of the claims appended hereto.

What is claimed as novel is as follows:

1. A fastener installation tool for installing blind fasteners of the type having a core pin, bearing surface forming means mounted to said core pin, a drive stem interconnected with said core pin, first tool engaging means disposed on one end of said core pin, and second tool engaging means disposed on one end of said bearing surface forming means whereby axial displacement of said core pin relative to said bearing surface forming means causes said bearing surface forming means to form a bearing surface and, upon formation of said bearing surface, causes said drive stem to separate from said core pin, said installation tool comprising:

first tool means engageable with said first tool engaging means;

second tool means engageable with said second tool engaging means;

means for axially displacing said first tool means relative to said second tool means in said engaged condition;

axial through passageway means formed in said first tool means, said axial through passageway means accepting said core pin therein when said first tool means engaged said first tool engaging means;

a first tool engagement member, said first tool means being formed at one end of said first tool engagement member; and receptacle means disposed adjacent the end of said first tool engagement member remote from said first tool engagement means, said receptacle means communicating with said axial through passageway means such as to permit entry therein of said drive stem after separation of said drive stem from said core pin.

2. The fastener installation tool of claim 1 further comprising means for automatically sequentially feeding blind fasteners into alignment with said first and second tool means.

3. The fastener installation tool of claim 2 wherein said feeding means further comprises:

belt means adapted to support a plurality of blind fasteners; and a transfer means movably interconnected with said belt means to advance said belt means relative to said first and second tool means to sequentially feed said blind fastener into alignment therewith.

4. The fastener installation tool of claim 1 further comprising:

a second tool member disposed coaxially with a first tool member, said second tool means being formed at one and thereof, said second tool member having an elongated cavity formed therein; and a first tool member disposed in said elongated cavity said first tool means being formed at one end thereof and said axial through passageway means comprising axial passageway from said one end to the other end thereof.

5. The fastener installation tool of claim 1 wherein said bearing surface forming means is threadably engaged with said core pin such that said bearing surface forming means is axially displaced relative to said core pin to form said bearing surface by relative rotation of said core pin and said bearing surface forming means, said fastener installation tool further comprising:

said first tool means comprising first wrenching means;

said second tool means comprising second wrenching means; and means for axial displacement comprises means for causing relative angular displacement of said first and second tool means.

6. The fastener installation tool of claim 5 further comprising means for automatically sequentially feeding blind fasteners into alignment with said first and second tool means.

7. The fastener installation tool of claim 5 further comprising:

a second tool member disposed coaxially with a first tool member, said second tool means being formed at one and thereof, said second tool member having an elongated cavity formed therein; and a first tool member disposed in said elongated cavity said first tool means being formed at one end thereof and said axial through passageway means comprising axial passageway from said one end to the other end thereof.

8. The fastener installation tool of claim 7 further comprising drive engagement means interconnected with one of said first and second tool member for rotatably driving said one tool member relative to the other tool member.

9. The fastener installation tool of claim 8 wherein said drive engagement means comprises a gear.

10. The fastener installation tool of claim 5 wherein said means for causing relative angular displacement comprises:

housing means fixedly interconnected with one of said first and second tool means;

rotational drive means mounted to said housing and providing an angular rotational output; and power transfer means interposed said rotational drive means and the other of said first and second tool means.

11. The fastener installation tool of claim 10 further comprising torsional spring means interposed said first and second tool means.

12. The fastener installation tool of claim 5 further comprising torsional spring means mechanically interposed said first and second tool means.

13. A fastener installation tool for installing blind fasteners of the type having a core pin, bearing surface forming means mounted to said core pin, a drive stem interconnected with said core pin, first tool engaging means disposed on one end of said core pin, and second tool engaging means disposed on one end of said bearing surface forming means whereby axial displacement of said core pin relative to said bearing surface forming means causes said bearing surface forming means to form a bearing surface and, upon formation of said bearing surface, causes said drive stem to separate from said core pin, said installation tool comprising:

first tool means engageable with said first tool engaging means;

second tool means engageable with said second tool engaging means:

means for axially displacing said first tool means relative to said second tool means in said engaged condition; and axial through passageway means formed in said first tool means, said axial through passageway means accepting said core pin therein when said first tool means engages said first tool engaging means;

and further comprising:

a first tool engagement member, said first tool means being formed at one end of said first tool engagement member; and receptacle means disposed adjacent the end of said first tool engagement member remote from said first tool engagement means, said receptacle means communicating with said axial through passageway means such as to permit entry therein of said drive stem after separation of said drive stem from said core pin; and, wherein said receptacle means comprises a hollow bottle removably interconnected with said first tool engagement member.

14. A fastener installation tool for installing blind fasteners of the type having a core pin, bearing surface forming means mounted to said core pin, a drive stem interconnected with said core pin, first tool engaging means disposed on one end of said core pin, and second tool engaging means disposed on one end of said bearing surface forming means whereby axial displacement of said core pin relative to said bearing surface forming means causes said bearing surface forming means to form a bearing surface and, upon formation of said bearing surface, causes said drive stem to separate from said core pin, said installation tool comprising:

first tool means engageable with said first tool engaging means;

second tool means engageable with said second tool engaging means;

means for axially displacing said first tool means relative to said second tool means in said engaged condition; and axial through passageway means formed in said first tool means, said axial through passageway means accepting said core pin therein when said first tool means engages said first tool engaging means:

wherein said bearing surface forming means is threadably engaged with said core pin such that said bearing surface forming means is axially displaced relative to said core pin to form said bearing surface by relative rotation of said core pin and said bearing surface forming means, said fastener installation tool further comprising:

said first tool means comprising first wrenching means;

said second tool means comprising second wrenching means; and said means for axial displacement comprises means for causing relative angular displacement of said first and second tool means:

and further comprising:

a first tool engagement member, said first tool means being formed at one end of said first tool engagement member; and receptacle means disposed adjacent the end of said first tool engagement member remote from said first tool engagement means, said receptacle means communicating with said axial through passageway means such as to permit entry therein of said drive stem after separation of said drive stem from said core pin; and wherein said receptacle means comprises a hollow bottle removably interconnected with said first tool engagement member.

* * * * *